United States Patent [19]

Lechtken et al.

[11] 4,324,744
[45] Apr. 13, 1982

[54] ACYLPHOSPHINE OXIDE COMPOUNDS

[75] Inventors: Peter Lechtken, Frankenthal; Ingolf Buethe, Mannheim; Anton Hesse, Luetzelsachsen, all of Fed. Rep. of Germany

[73] Assignee: BASF Aktiengesellschaft, Fed. Rep. of Germany

[21] Appl. No.: 148,221

[22] Filed: May 9, 1980

Related U.S. Application Data

[63] Continuation of Ser. No. 55,360, Jul. 6, 1979, abandoned.

[30] Foreign Application Priority Data

Jul. 14, 1978 [DE] Fed. Rep. of Germany ....... 2830927

[51] Int. Cl.³ ............................ C07F 9/30; C07F 9/38; C07F 9/53
[52] U.S. Cl. .................................... 260/932; 260/941; 546/21; 549/6; 568/15
[58] Field of Search .............. 546/21; 549/6; 260/941; 260/932; 568/15

[56] References Cited

U.S. PATENT DOCUMENTS 3,826,640 7/1974 Theissen ................................. 71/86

OTHER PUBLICATIONS

Laskorin et al., Chemical Abstracts, vol. 82, No. 3, 16, 899d, Jan. 20, 1975.
Musierowicz et al., Chemical Abstracts, vol. 88, No. 25, 189, 901a, Jun. 19, 1978.

*Primary Examiner*—Alan L. Rotman
*Attorney, Agent, or Firm*—Keil & Witherspoon

[57] ABSTRACT

Acylphosphine oxide compounds of the general formula

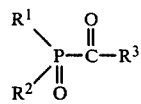

where $R^1$ is alkyl, cyclohexyl, cyclopentyl, aryl which is unsubstituted or substituted by halogen, alkyl or alkoxy, or an S-containing or N-containing five-membered or six-membered heterocyclic radical, $R^2$ has one of the meanings of $R^1$ (but $R^1$ and $R^2$ may be identical or different), or is alkoxy, aryloxy or aralkoxy, or $R^1$ and $R^2$ together from a ring, and $R^3$ is straight-chain or branched alkyl of 2 to 18 carbon atoms, a cycloaliphatic radical of 3 to 12 carbon atoms, phenyl or naphthyl which are alkyl-, alkoxy- or thioalkoxy-substituted, or an S-containing or N-containing five-membered or six-membered heterocyclic radical, and may contain additional functional groups, or is the group

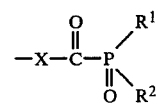

where $R^1$ and $R^2$ have the above meanings and X is phenyl or an aliphatic or cycloaliphatic divalent radical of 2 to 6 carbon atoms, and one or more of the radicals $R^1$ to $R^3$ may be olefinically unsaturated, a process for the preparation of these acylphosphine oxide compounds from acid halides of the general formula

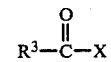

where X is chlorine or bromine, and a phosphine of the general formula

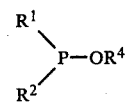

and the use of the acylphosphine oxides as photoinitiators in photopolymerizable compositions.

3 Claims, No Drawings

ACYLPHOSPHINE OXIDE COMPOUNDS

This is a continuation, of application Ser. No. 55,360, filed July 6, 1979, now abandoned.

The present invention relates to novel acylphosphine oxide compounds, to their preparation and to their use as photoinitiators in photopolymerizable compositions.

A plurality of photoinitiators having various structures has been disclosed, for example benzil dimethyl ketal (German Laid-Open Application DOS No. 2,261,383), benzoin ethers (German Laid-Open Application DOS No. 1,694,149), and thioxanthones (German Laid-Open Application DOS No. 2,003,132).

However, photopolymerizable compositions hardened with such initiator systems exhibit an undesirable yellowing, which makes the systems unusable on pale (or white) substrates or as a finish on true-to-color reproductions.

The present invention relates to acylphosphine oxide compounds of the general formula

where $R^1$ is straight-chain or branched alkyl of 1 to 6 carbon atoms, cyclohexyl, cyclopentyl, aryl which is unsubstituted or substituted by halogen, alkyl or alkoxy, or an S-containing or N-containing five-membered or six-membered heterocyclic radical, $R^2$ has one of the meanings of $R^1$ (but $R^1$ and $R^2$ may be identical or different), or is alkoxy of 1 to 6 carbon atoms, aryloxy or aralkoxy, or $R^1$ and $R^2$ together form a ring, and $R^3$ is straight-chain or branched alkyl of 2 to 18 carbon atoms, a cycloaliphatic radical of 3 to 12 carbon atoms, phenyl or naphthyl which are substituted by alkyl, alkoxy or thioalkoxy, or an S-containing or N-containing five-membered or six-membered heterocyclic radical, and may contain additional functional groups, or is the group

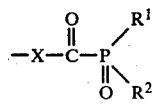

where $R^1$ and $R^2$ have the above meanings and X is phenylene or an aliphatic or cycloaliphatic divalent radical of 2 to 6 carbon atoms, and one or more of the radicals $R^1$ and $R^3$ may be olefinically unsaturated.

The present invention further relates to a process for the preparation of the acylphosphine oxide compounds according to the invention, and to their use as photoinitiators in photopolymerizable compositions.

The following details may be noted with regard to the general formula (I) of the acylphosphine oxide compounds according to the invention:

$R^1$ may be straight-chain or branched alkyl of 1 to 6 carbon atoms, eg. methyl, ethyl, i-propyl, n-propyl, n-butyl, amyl or n-hexyl, cyclopentyl, cyclohexyl, aryl, eg. phenyl and naphthyl, halogen-substituted aryl, eg. monochlorophenyl and dichlorophenyl, alkylsubstituted phenyl, eg. methylphenyl, ethylphenyl, isopropylphenyl, tert.-butylphenyl and dimethylphenyl, alkoxysubstituted aryl, eg. methoxyphenyl, ethoxyphenyl and dimethoxyphenyl, or an S-containing or N-containing five-membered or six-membered ring, eg. fully unsaturated thienyl, or pyridyl, $R^2$ may have one of the meanings of $R^1$ and may also be alkoxy of 1 to 6 carbon atoms, eg. methoxy, ethoxy, i-propoxy, butoxy or ethoxyethoxy, or aryloxy, eg. phenoxy, methylphenoxy or benzyloxy, and $R^1$ and $R^2$ may be joined to form a ring, as, for example, in acylphosphonic acid o-phenylene esters.

$R^3$ may be for example ethyl, i-propyl, n-propyl, n-butyl, i-butyl, tert.-butyl, i-amyl, n-hexyl, heptyl, n-octyl, 2-ethylhexyl, i-nonyl, dimethylheptyl, lauryl, stearyl, cyclopropyl, cyclobutyl, cyclopentyl, 1-methylcyclopentyl, cyclohexyl, 1-methylcyclohexyl, norbornadienyl, adamantyl, dimethyloctyl, dimethylnonyl, dimethyldecyl, methylphenyl, dimethylphenyl, trimethylphenyl, tert.-butylphenyl, isopropylphenyl, methoxyphenyl, dimethoxyphenyl, i-propoxyphenyl, thiomethoxyphenyl, α- and β-naphthyl, thienyl, pyridyl, α-acetoxyethyl or β-carboxyethyl.

$R^1$, $R^2$ and $R^3$ may in addition contain carbon-carbon double bonds which allow the photoinitiator to be incorporated into the binder as copolymerized units.

Examples of the acylphosphine oxide compounds according to the invention are: methyl isobutyryl-methylphosphinate, methyl isobutyryl-phenylphosphinate, methyl pivaloylphenylphosphinate, methyl 2-ethylhexanoyl-phenylphosphinate, isopropyl pivaloyl-phenylphosphinate, methyl p-toluylphenylphosphinate, methyl o-toluyl-phenylphosphinate, methyl 2,4-dimethylbenzoyl-phenylphosphinate, isopropyl p-tert.-butylphenylphosphinate, methyl pivaloyl-(4-methylphenyl)-phosphinate, vinyl pivaloyl-phenylphosphinate, methyl acryloyl-phenylphosphinate, isobutyryl-diphenylphosphine oxide, pivaloyl-diphenylphosphine oxide, 1-methyl-1-cyclohexanoyl-diphenylphosphine oxide, 2-ethylhexanoyl-diphenylphosphine oxide, p-toluyl-diphenylphosphine oxide, o-toluyldiphenylphosphine oxide, p-tert.-butyldiphenylphosphine oxide, 3-pyridylcarbonyl-diphenylphosphine oxide, acryloyldiphenylphosphine oxide, benzoyl-diphenylenephosphine oxide, 2,2-dimethyl-heptanoyl-diphenylphosphine oxide, terephthaloyl-bis-diphenylphosphine oxide and adipoyl-bis-diphenylphosphine oxide.

These compounds may be prepared by reacting an acid halide of the formula

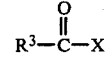

where X is Cl or Br, with a phosphine of the formula

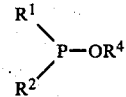

where $R^4$ is straight-chain or branched alkyl of 1 to 6 carbon atoms, or cycloalkyl of 5 or 6 carbon atoms.

The reaction can be carried out in a solvent, for example a hydrocarbon or hydrocarbon mixture, eg. petroleum ether, toluene, cyclohexane, an ether or some other conventional inert organic solvent, or even without a solvent, at from $-30°$ C. to $+110°$ C., preferably at from 10° to 70° C. The product can be directly crystallized out from the solvent, or remains after evaporation, or is distilled under reduced pressure.

The acid halide $$R^3\overset{\overset{O}{\|}}{C}X$$

and the substituted phosphine $R^1R^2POR^4$ are obtained by processes known to those skilled in the art from the literature (for example Weygand-Hilgetag, Organisch-Chemische Experimentierkunst, 4th edition, pages 246–256, J. A. Barth-Verlag, Leipzig 1970 and K. Sasse in Houben-Weyl, volume 12/1, pages 208–209, G. Thieme-Verlag, Stuttgart).

The process for the preparation of the compounds according to the invention can for example be represented by the following equation:

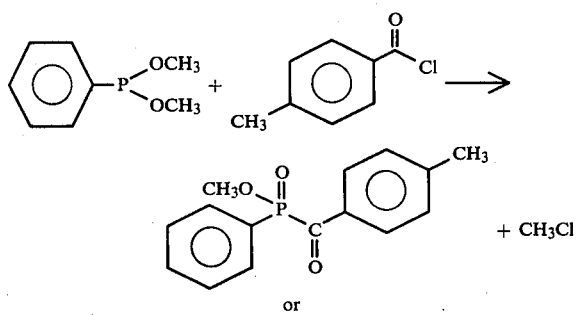

Examples of suitable phosphines are methyldimethoxyphosphine, butyldimethoxyphosphine, phenyldimethoxyphosphine, tolydimethoxyphosphine, phenyldiethoxyphosphine, tolydiethoxyphosphine, phenyldiisopropoxyphosphine, tolydiisopropoxyphosphine, phenyldibutoxyphosphine, tolyldibutoxyphosphine and dimethylmethoxyphosphine, dibutylmethoxyphosphine, dimethylbutoxyphosphine, diphenylmethoxyphosphine, diphenylethoxyphosphine, diphenylpropoxyphosphine, diphenylisopropoxyphosphine, diphenylbutoxyphosphine and similar starting materials which lead to the compounds according to the invention.

Suitable acid halides are the chlorides and bromides, of which the former are particularly preferred.

Specific examples of the compounds according to the invention (without this list implying any restriction) are:

TABLE 1

Examples of compounds according to the invention (Ph = phenyl)

| Compound | M.p. | B.p. | Yield | Analysis | C | H | P |
|---|---|---|---|---|---|---|---|
| CH₃–C(CH₃)(CH₃)–C(=O)–P(Ph)(=O)(OCH₃) | — | 104/0.3mm | 65% | calc.<br>found | 60.0<br>59.8 | 7.08<br>6.9 | 12.9<br>12.4 |
| CH₃–CH₂–CH₂–CH₂–CH(CH₂CH₃)–C(=O)–P(Ph)(=O)(OCH₃) | — | 164/1.2mm | 65% | calc.<br>found | 64.06<br>63.8 | 7.83<br>8.1 | 11.03<br>11.0 |
| CH₃–C₆H₄–C(=O)–P(Ph)(=O)(OCH₃) | 101 | — | 70% | calc.<br>found | 65.69<br>65.7 | 5.47<br>5.6 | 11.31<br>11.0 |
| H₃C–C₆H₄–C(=O)–P(Ph)(Ph)(=O) | 105 | — | 73% | calc.<br>found | 75.00<br>75.30 | 5.31<br>5.8 | 9.69<br>9.3 |
| 2-CH₃–C₆H₄–C(=O)–P(Ph)(Ph)(=O) | 107 | — | 84% | calc.<br>found | 75.00<br>74.7 | 5.31<br>5.4 | 9.69<br>9.5 |
| (CH₃)₃C–C₆H₄–C(=O)–P(Ph)(Ph)(=O) | 136 | — | 83% | calc.<br>found | 76.24<br>76.0 | 6.35<br>6.5 | 8.56<br>8.7 |

TABLE 1-continued

Examples of compounds according to the invention (Ph = phenyl)

| Compound | M.p. | B.p. | Yield | Analysis | | | |
|---|---|---|---|---|---|---|---|
| | | | | | C | H | P |
| Ph₂P(O)–C(O)–C₆H₄–C(O)–PPh₂(O) | 205 | — | 35% | calc. | 71.91 | 4.49 | 11.61 |
| | | | | found | 71.8 | 4.8 | 11.0 |
| (CH₃)₃C–C(O)–P(O)Ph₂ | 114 | — | 81% | calc. | 71.33 | 6.64 | 10.84 |
| | | | | found | 71.0 | 6.5 | 11.0 |
| (CH₃)₃C–C(O)–P(O)(OCH(CH₃)₂)(Ph) | — | 120°/0.5mm | 60% | calc. | 62.68 | 7.84 | 11.57 |
| | | | | found | 63.0 | 8.0 | 11.4 |
| CH₃CH₂CH₂CH₂C(CH₃)(CH₃)–C(O)–P(O)Ph₂ | — | — | 90% | calc. | 73.68 | 7.89 | 9.06 |
| | | | | found | 73.6 | 8.1 | 8.6 |
| CH₃–C(O)–O–CH₂–C(CH₃)₂–C(O)–P(O)Ph₂ | — | — | 90% | calc. | 66.28 | 6.11 | 9.01 |
| | | | | found | 65.9 | 6.1 | 8.6 |
| (CH₃)₃C–C(O)–P(O)(OCH(CH₃)₂)(CH₃) | — | 51°/0.3mm | 80% | calc. | 52.43 | 9.22 | 15.05 |
| | | | | found | 52.1 | 9.1 | 14.9 |
| Naphthyl–C(O)–P(O)Ph₂ | 166 | — | 65% | calc. | 77.52 | 4.78 | 8.71 |
| | | | | found | 77.7 | 4.8 | 8.4 |
| CH₃–C₆H₄–C(O)–P(O)(OC₂H₅)(CH₃) | — | 102°/0.05mm | 60% | calc. | 58.41 | 6.64 | 13.71 |
| | | | | found | 58.9 | 6.7 | 13.5 |
| Cyclohexyl–CH(CH₃)–C(O)–P(O)Ph₂ | 80 | — | 26% | calc. | 73.62 | 7.06 | 9.51 |
| | | | | found | 73.3 | 7.1 | 9.6 |
| CH₃CH₂CH₂CH₂C(CH₃)(CH₂OCH₃)–C(O)–P(O)Ph₂ | — | — | 90% | calc. | 73.68 | 7.89 | 9.06 |
| | | | | found | 73.9 | 8.1 | 9.4 |

The compounds having the structure according to the invention exhibit very good reactivity when used as photoinitiators for photopolymerizable monomers possessing one or more carbon-carbon multiple bonds, and for mixtures of such monomers with one another and with conventional adjuvants. The acylphosphine oxide compounds according to the invention are particularly suitable for use as photoinitiators in photopolymerizable compositions for surface coatings and finishes. In respect of yellowing of the finishes and surface coatings thus obtained they are far superior to conventional photoinitiators (for example benzil dimethylketal).

Particularly preferred compounds are acyl-phenyl-phosphinic acid esters and acyl-diphenyl-phosphine oxides where acyl is derived from a secondary-substituted or tertiary-substituted aliphatic carboxylic acid, eg. pivalic acid, 1-methylcyclohexanecarboxylic acid, norbornenecarboxylic acid, α,α-dimethylalkanecarboxylic acids (Versatic ®-acid of 9 to 13 carbon atoms) or 2-ethylhexanecarboxylic acid, or from a substituted aromatic carboxylic acid., e.g. p-methylbenzoic acid, o-methylbenzoic acid, 2,4-dimethylbenzoic acid, p-tert.-butylbenzoic acid, 2,4,5-trimethylbenzoic acid, p-methoxybenzoic acid or p-thiomethylbenzoic acid.

Suitable photopolymerizable monomers are the conventional compounds and materials possessing polymerizable carbon-carbon double bonds which are activated by, for example, aryl, carbonyl, amino, amido, ester, carboxyl or cyanide groups, by halogen atoms or by additional carbon-carbon double bonds and triple bonds. Examples are vinyl ethers and vinyl esters, styrene, vinyltoluene, acrylic acid and methacrylic acid and their esters with monohydric and polyhydric alcohols, their nitriles and their amides, maleic acid esters and fumaric acid esters, N-vinylpyrrolidone, N-vinylcaprolactam, N-vinylcarbazole and allyl esters, eg. diallyl phthalate.

Examples of suitable polymerizable compounds of higher molecular weight are unsaturated polyesters, prepared from α,β-unsaturated dicarboxylic acids, eg. maleic acid, fumaric acid or itaconic acid, which may or may not be mixed with saturated or aromatic dicarboxylic acids, eg. adipic acid, phthalic acid or terephthalic acid, by reaction with alkanediols, eg. ethylene glycol, propylene glycol, butanediol, neopentylglycol or oxyalkylated bisphenol A, epoxide-acrylates, prepared from acrylic acid or methacrylic acid and aromatic or aliphatic diglycidyl ethers, urethaneacrylates (for example prepared from hydroxy alkylacrylates and polyisocyanates) and polyester-acrylates (for example prepared from hydroxyl-containing saturated polyesters and acrylic acid or methacrylic acid).

The photopolymerizable compounds, whose composition for any particular end use is familiar to those skilled in the art, may be mixed, in the conventional manner, with saturated and/or unsaturated polymers and with other adjuvants, for example thermal polymerization inhibitors, paraffin, pigments, dyes, peroxides, levelling agents, fillers, glass fibers and stabilizers against thermal or photochemical degradation.

Such mixtures are known to those skilled in the art, and the nature and amount of the additives depend on the particular end use.

The compounds according to the invention are in general employed in a concentration of from 0.01 to 15%, preferably from 0.1 to 5%, based on the photopolymerizable composition. They may also be combined with accelerators, which overcome the inhibiting effect of atmospheric oxygen on the photopolymerization.

Examples of such accelerators or synergistic agents are secondary and/or tertiary amines, eg. methyldiethanolamine, dimethylethanolamine, triethylamine, triethanolamine, ethyl p-dimethylaminobenzoate, benzyldimethylamine, dimethylaminoethyl acrylate, N-phenylglycine, N-methyl-N-phenylglycine and analogous compounds known to those skilled in the art. Aliphatic and aromatic halides, eg. 2-chloromethyl-naphthalene and 1-chloro-2-chloromethyl-naphthalene, and compounds which form free radicals, eg. peroxides and azo compounds, may also be used to accelerate the hardening.

The radiation sources used to provide the light which initiates the polymerization of such mixtures are those which preferably emit light in the absorption region of the compounds according to the invention, ie. from 230 to 450 nm. Low-pressure, medium-pressure and high-pressure mercury lamps, superactinic fluorescent tubes or pulse lamps are particularly suitable. The said lamps may or may not be doped.

In the Examples which follow, parts and percentages are by weight, unless stated otherwise. Parts by volume bear the same relation to parts as that of the liter to the kilogram.

EXAMPLE 1

225 parts of diphenylchlorophosphine, dissolved in 220 parts by volume of petroleum ether, are added to a mixture of 1,350 parts by volume of petroleum ether (boiling range 40°–70° C.), 180 parts by volume of N,N-diethylaniline and 67 parts by volume of methanol at 0° C., whilst stirring. The mixture is then stirred for a further 2 hours at room temperature. After cooling the mixture to about +5° C., the amine hydrochloride which has separated out is filtered off and the filtrate is first distilled at 10–20 mm Hg, to remove all low-boiling material. The methoxy-diphenylphosphine is then fractionally distilled at 0.1–1 mm Hg. Boiling point 120°–124° C./0.5 mm Hg. Yield: 175 parts (80%, based on diphenylchlorophosphine).

64.8 parts of methoxy-diphenylphosphine are added dropwise to 36.2 parts of pivaloyl chloride at 30°–60° C., whilst stirring. After completion of the addition, the reaction is allowed to continue for 30 minutes, the mixture is then cooled to 0°–10° C., and the product which has precipitated is recrystallized from cyclohexane.

Yield: 69.5 parts of pivaloyldiphenylphosphine oxide (81% of theory).

Melting point 110°–112° C.

NMR (CDCl$_3$, δ): 1.33 (s), 7.4–8.0 (m).

Analysis C$_{17}$H$_{19}$O$_3$P (286) Calculated: C 71.33; H 6.64; P 10.84. Found: C 70.0; H 6.5; P 11.0.

EXAMPLE 2

108 parts of methoxydiphenylphosphine (prepared as described in Example 1), dissolved in 200 parts by volume of toluene are added to 77 parts of toluic acid chloride. The mixture is then heated for 60 minutes at 50° C., after which it is cooled and the precipitate of toluyldiphenylphosphine oxide is filtered off and recrystallized from cyclohexane.

Yield 117 parts (73% of theory). Melting point 105° C.

NMR (CDCl$_3$, δ): 235 (s), 7.2–8 (m).

Analysis C$_{20}$H$_{17}$O$_2$P (320) Calculated: C 75.00; H 5.31; P 9.69. Found: C 75.3; H 5.8; P 9.3.

EXAMPLE 3

Using a method similar to that of Example 2, 77 parts of 2-methyl-benzoic acid chloride and 108 parts of methoxydiphenylphosphine give 134 parts of 2-methylbenzoyldiphenylphosphine oxide. Yield 84% of theory, melting point 107° C.

NMR (CDCl$_3$, δ): 2.5 (s), 7.2–8 (m), 8.8 (m).

Analysis for C$_{20}$H$_{17}$O$_2$P (320) Calculated: C 75.0; H 5.31; P 9.69. Found: C 74.7; H 5.4; P 9.5.

EXAMPLE 4

Using a method similar to that of Example 1, 41.3 parts of p-tert.-butylbenzoic acid chloride are reacted with 45.4 parts of methoxydiphenylphosphine, dissolved in 20 parts of toluene, in 90 minutes at 50° C. After evaporating off the solvent on a rotary evaporator, the product is recrystallized from cyclohexane.

Yield: 63 parts (83% of theory). Melting point 136° C.

NMR (CDCl$_3$, δ): 1.3 (s), 7.3–8.1 (m), 8.5 (d).

Analysis C$_{23}$H$_{23}$O$_2$P (362) Calculated: C 76.24; H 6.35; P 8.56. Found: C 76.0; H 6.5; P 8.7.

EXAMPLE 5

Using a method similar to that of Example 2, 52 parts of terephthalic acid dichloride, dissolved in 200 parts of toluene, and 108 parts of methoxydiphenylphosphine give 46 parts of terephthaloyl-bis-diphenylphosphine oxide (yield 35% of theory). Melting point 205° C.

NMR (CDCl$_3$, δ): 6.8–8.2 (m).

Analysis C$_{32}$H$_{24}$O$_4$P$_2$ (534) Calculated: C 71.91; H 4.49; P 11.61. Found: C 71.8; H 4.8; P 11.0.

EXAMPLE 6

Using a method similar to that of Example 2, 80 parts of 1-methyl-1-cyclohexanecarboxylic acid chloride and 108 parts of methoxydiphenylphosphine, in the absence of a solvent, give 100 parts of 1-methyl-cyclohexylcarbonyl-diphenylphosphine oxide as an oily crude product, which is purified by chromatography over silica gel (using toluene as the eluant).

Yield: 42 parts (26% of theory). Melting point 80° C.
NMR (CDCl$_3$, δ): 14 (s); 1.1–1.6 (m); 2.1–2.4 (m); 7.3–8.0 (m).
Analysis C$_{20}$H$_{23}$O$_2$P (326) Calculated: C 73.62; H 7.06; P 9.51. Found: C 73.3; H 7.1; P 9.6.

EXAMPLE 7

Using a method similar to that of Example 1, 88 parts of 2-methyl-2-ethylhexanoic acid chloride and 108 parts of methoxydiphenylphosphine give 165 parts of 2-methyl-2-ethylhexanoyl-diphenylphosphine oxide as an oily crude product. Column chromatography over silica gel (eluant: a 3:1 mixture of toluene and ether) gives the product as a pale yellowish oil. Yield 154 parts (90% of theory).

NMR (CDCl$_3$, δ): 1.2 (s), 0.5–2.2 (m), 7.3–8.1 (m).
Analysis C$_{21}$H$_{27}$O$_2$P (342) Calculated: C 73.68; H 7.89; P 9.06. Found: C 73.9; H 8.1; P 9.4.

EXAMPLE 8

Using a method similar to that of Example 1, 43.2 parts of methoxydiphenylphosphine are added dropwise, at 50° C., to 35.3 parts of 2,2-dimethyl-heptanecarboxylic acid chloride (Versatic ®-acid chloride). The mixture is stirred for 3 hours at 50° C., then cooled to 15° C. and stirred into a slurry of 60 g silica gel in 350 ml of toluene; stirring is then continued for one hour whilst cooling with ice. The mixture is then filtered and the solvent is distilled off under reduced pressure. Versatoyl-diphenylphosphine oxide remains as a viscous oil.

Yield: 62 parts (90% of theory).
NMR (CDCl$_3$, δ): 0.4–2.3 (m), 7.2–8.1 (m).
Analysis C$_{21}$H$_{27}$O$_2$P (342) Calculated: C 73.68; H 7.89; P 9.06. Found: C 73.6; H 8.1; P 8.6.

EXAMPLE 9

143 parts of phenyldichlorophosphine are added dropwise in the course of one hour to a mixture of 600 parts by volume of petroleum ether, 263 parts of N,N-diethylaniline and 120 parts of isopropanol at 0° C. The mixture is then stirred for 1 hour at room temperature, worked up as described in Example 1 and distilled. Diisopropoxy-phenylphosphine distils at 68°–72° C./0.3 mm Hg. Yield: 126 parts (69% of theory).

158 parts of diisopropoxyphenylphosphine are added slowly to 84 parts of pivaloyl chloride at 50°–60° C., with thorough stirring. Stirring is then continued for two hours, after which the mixture is fractionated under reduced pressure. Isopropyl pivaloyl-phenylphosphinate distils at 119°–121° C./0.5 mm.

Yield: 112 parts (60% of theory).
NMR (CDCl$_3$, δ) 1.25 (s); 1.33 (t); 4.5 (m); 7.3–8 (m).
Analysis: C$_{14}$H$_{21}$O$_3$P (268) Calculated: C 62.68; H 7.84; P 11.57. Found: C 63.0; H 8.0; P 11.4.

EXAMPLE 10

214 parts of phenyldichlorophosphine are added to a mixture of 1,000 parts by volume of toluene, 421 parts by volume of N,N-diethylaniline and 100 parts by volume of methanol at 0° C. The mixture is then stirred for 1 hour at room temperature, the amine hydrochloride precipitate is filtered off and the filtrate is fractionated. Dimethoxyphenylphosphine distils at 46°–50° C./0.2–0.3 mm Hg.

Yield: 190 parts (93% of theory).

110.5 parts of dimethoxyphenylphosphine are added dropwise at 15° C. to 78.7 parts of pivaloyl chloride. The reaction mixture is then heated for 30 minutes at 50° C., after which it is distilled. Methyl pivaloyl-phenylphosphinate passes over at 104°–107° C./0.3 mm Hg.

Yield: 101.3 parts (65% of theory).
NMR (CDCl$_3$, δ): 1.3 (s); 3.75 (d); 7.4–8 (m).
Analysis: C$_{12}$H$_{17}$O$_3$P (240): Calculated: C 60.0; H 7.08; P 12.9. Found: C 59.8; H 6.9; P 12.4.

EXAMPLE 11

170 parts of dimethoxyphenylphosphine (Example 4) are added dropwise to 163 parts of 2-ethylhexanoic acid chloride at 30° C. The mixture is then stirred for 50 minutes at 50° C., after which it is fractionated under reduced pressure from an oil pump.

Methyl 2-ethyl-hexanoyl-phenylphosphinate passes over at 160°–168° C./1.2 mm.

Yield: 230 parts (81% of theory).
NMR (CDCl$_3$, δ): 0.6–2 (m), 3.2 (q), 3.8 (d), 7.3–8 (m).
Analysis: C$_{15}$H$_{22}$O$_3$P (281) Calculated: C 64.06; H 7.83; P 11.03. Found: C 63.8; H 8.1; P 11.0.

EXAMPLE 12

170 parts of dimethoxyphenylphosphine are added to 155 parts of 4-methylbenzoyl chloride, dissolved in 250 parts by volume of toluene, at 30° C. The reaction is allowed to continue for 60 minutes, after which the mixture is cooled to 0° C. and the precipitate is filtered off. After recrystallization from cyclohexane, methyl 4-methylbenzoyl-phenylphosphinate melts at 99°–101° C.

Yield: 180 parts (65% of theory).
NMR: 2.25 (s), 3.7 (d), 7–8.1 (m).
Analysis: C$_{15}$H$_{15}$O$_3$P (274) Calculated: C 65.69; H 5.47; P 11.31. Found: C 65.7; H 5.6; P 11.0.

EXAMPLE 13

A hiding pigmented finish is prepared from a mixture of 100 parts of the reaction product of bisphenol A diglycidyl ether and 2 moles of acrylic acid, 122 parts of butane-1,4-diol diacrylate, 6 parts of n-butanol and 122 parts of TiO$_2$ pigment. Finishes of this type are known to those skilled in the art. 6.5 parts of 2-methylbenzoyl-diphenylphosphine oxide are added, as a photoinitiator, to this mixture. The finish formulated in this way is applied, as a 75 μm thick layer, to a glass plate by means of a knife coater and is irradiated with a Hg high-pressure lamp (having a power of 80 W/cm of arc length). The distance from lamp to film is 10 cm. The samples are drawn past the lamp, in an inert gas atmosphere, on a conveyor belt having a continuously variable speed adjustment.

At conveyor belt speeds of up to 6 m/min, scratch-resistant, fully hardened and completely white films are obtained.

EXAMPLE 14

Three parts of one of various photoinitiators are added to a binder comprising 65 parts of a reaction product of bisphenol A diglycidyl ether with two equivalents of acrylic acid and 35 parts of butane-1,4-diol diacrylate. An 80 μm thick film of the mixture is spread on a glass plate by means of a knife coater, and is irradiated (Hg high-pressure lamp, 80 W/cm of arc length, distance 10 cm). The irradiation time required to give a nail-hard, scratch-resistant surface is shown in terms of the maximum possible conveyor belt speed at which the samples can be drawn past the lamp and still give this result. For example, the following values were measured:

TABLE 2

Hardening activity of the photoinitiators

| Initiator | Maximum conveyor belt speed in m/min | | |
|---|---|---|---|
| | In air | In inert gas | In air; 3% of N-phenylglycine added to the mixture |
| Diethyl pivaloylphosphonate | — | 10 | |
| Methyl pivaloylphenylphosphinate | 10 | 150 | 10 |
| Methyl toluyl-phenylphosphinate | 10 | 70 | 25 |
| Methyl 2-ethylhexanoyl-phenylphosphinate | — | 40 | |
| Toluyl-diphenylphosphine oxide | — | 70 | 25 |
| 2-Methylbenzoyl-diphenylphosphine oxide | — | 70 | |
| Pivaloyl-diphenylphosphine oxide | 11 | 150 | 25 |

EXAMPLE 15

3% of N-phenylglycine are added to a finish, prepared as described in Example 14, which is then spread on glass plates, as in Example 14, and irradiated. The results are shown in Table 2.

EXAMPLE 16

An unsaturated polyester is prepared by esterifying 431 parts of maleic anhydrides and 325 parts of phthalic anhydride with 525 parts of 1,2-propylene glycol. After adding 0.01% of hydroquinone, a 66 percent strength solution of the polyester in styrene is prepared. 1.5 parts of pivaloyl-diphenylphosphine oxide are added to 97 parts of this unsaturated polyester resin.

For the light-hardening experiments, 10 parts of a 1 percent strength solution of paraffin (softening range 50°-52° C.) in styrene are added to 100 parts of this mixture, and the resin is applied to a glass plate, using a film spreader with 400 m clearance. After air-drying for about one minute, the films are exposed to fluorescent lamps (Phillips TLA 05/40 W) mounted at a distance of 4 cm.

After an exposure time of 4 minutes, the films have a König pendulum hardness of 76 s and can be rubbed down and buffed.

EXAMPLE 17

A binder prepared as described in Example 14 is mixed with three parts of one of the photoinitiators of Table 2, and a white photographic paper is then coated with a 75 μm film of the mixture and drawn, under inert gas, past a Hg high-pressure lamp (power 80 W/cm of arc length) at a speed of 72 m/min. The samples hardened in this way are nail-hard and very glossy. As is shown in Table 3, the compounds according to the invention far surpass in respect of yellowing the prior art compounds, of which benzil dimethylketal and a benzil dimethylketal/benzophenone/methyldiethanolamine mixture were taken as typical.

TABLE 3

Yellowing of photopolymerized finishes

| Initiator | Concentration employed | Yellowing measured in terms of the yellowness index+ |
|---|---|---|
| Benzil dimethylketal | 3% | 9.20 |
| Benzil dimethylketal/benzophenone/methyldiethanolamine (2:1:3) | 6% | 8.15 |
| Pivaloyl-diphenylphosphine oxide | 3% | −3.33 |
| p-Toluyl-diphenylphosphine oxide | 3% | −3.72 |
| Methyl pivaloyl-phenylphosphinate | 3% | −2.34 |

+Yellowness index according to ASTM D 1925-G7 measured with a Zeiss DMC 25 instrument.

EXAMPLE 18

To measure the hardening activity of the compounds according to the invention in photopolymerizable unsaturated polyester resins, the variation in temperature during irradiation was recorded. The following resins were prepared for these experiments.

Resin A: Melt condensation of maleic acid, o-phthalic acid, ethylene glycol and 1,2-propylene glycol in the molar ratio of 1:2:2.4:0.85 gives an unsaturated polyester having an acid number of 50.

Resin B: Maleic acid, tetrahydrophthalic acid and diethylene glycol in a molar ratio of 1:0.5:1.5 give an unsaturated polyester resin having an acid number of 46.

For use, a 65 percent strength solution of each resin in styrene is prepared and stabilized with 100 ppm of hydroquinone.

10 g of a resin are stabilized with 0.35% of the particular photoinitiator and then irradiated in a tin-plate dish (diameter 3.8 cm) embedded in rigid polyurethane foam to provide heat insulation. The radiation source used is a UV battery (87×49 cm) of ten lamps arranged alongside one another (TUV 40 W/0.5, Phillips; the distance from lamp to sample is 10 cm). The temperature variation in the resin during hardening is recorded by means of a thermocouple connected to a pen recorder. The values measured are summarized in Table 4.

TABLE 4

Temperature variation during photopolymerization

| Photoinitiator | Concentration | Resin | Hardening time (time between 25° C. and $T_{max}$) | Maximum temperature reached by sample, $T_{max}$ (°C.) |
|---|---|---|---|---|
| Methyl pivaloyl-phenylphos- | 0.35% | A | 18 min 15 s | 106 |

TABLE 4-continued

| | Temperature variation during photopolymerization | | | |
|---|---|---|---|---|
| Photoinitiator | Concentration | Resin | Hardening time (time between 25° C. and $T_{max}$) | Maximum temperature reached by sample, $T_{max}$ (°C.) |
| phinate | 0.35% | B | 13 min | 112 |
| | 0.35% | A | 15 min 15 s | 122 |
| Toluyl-diphenylphosphine oxide | 0.35% | B | 10 min 5 s | 133 |
| 4-tert.-Butyl-benzoyldiphenyl-phosphine oxide | 0.35% | A | 14 minn 55 s | 120 |
| Terephthaloyl-bis-diphenyl-phosphine oxide | 0.35% | A | 21 min 15 s | 109 |

We claim:
1. An acylphosphine oxide compound of the formula

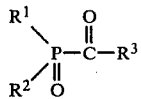 (I)

where $R^1$ is straight-chain or branched alkyl of 1 to 6 carbon atoms, cyclohexyl, cyclopentyl, phenyl or naphthyl which are unsubstituted or substituted by halogen, alkyl of 1 to 6 carbon atoms or alkoxy of 1 to 6 carbon atoms, a pyridyl or thienyl radical, $R^2$ has one of the meanings of $R^1$ or is alkoxy of 1 to 6 carbon atoms, phenoxy, methylphenoxy, benzyloxy or vinyloxy, or $R^1$ and $R^2$ may be joined together to form a five- or six-membered P-containing ring, and $R^3$ is straight-chain or branched alkyl of 2 to 18 carbon atoms, a cyclopropyl, cyclobutyl, cyclopentyl, 1-methylcyclopentyl, cyclohexyl, 1-methylcyclohexyl, norbornadienyl, adamantyl, vinyl, methylvinyl, naphthyl radical, phenyl or naphthyl which are substituted by alkyl of 1 to 8 carbon atoms or by thioalkoxy of 1 to 6 carbon atoms, a naphthyl which is substituted by alkoxy of 1 to 6 carbon atoms, a pyridyl or thienyl radical, and may contain additional functional groups, or is the group

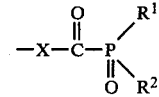

where $R^1$ and $R^2$ have the above meanings and X is phenylene or butane-1,4-diyl with the proviso that $R^1$ is not t-butyl or benzyl if $R^3$ stands for t-butyl or n-butyl.

2. An acylphosphine oxide compound as set forth in claim 1, wherein $R^3$ is a tertiary alkyl radical of 4 to 18 carbon atoms.

3. An acylphosphine oxide compound as set forth in claim 1, wherein $R^3$ is mono-, di- or tri-alkyl-substituted phenyl, each alkyl being of 1 to 8 carbon atoms.

* * * * *